United States Patent [19]
Kim et al.

[11] Patent Number: 6,025,396
[45] Date of Patent: Feb. 15, 2000

[54] STABLE PROSTAGLANDIN E1-CONTAINING INJECTABLE COMPOSITION

[75] Inventors: Chul Kim; Sung Tae Lee, both of Seoul; Seung Kyun Roh, Ansan; Eung Bae Kim, Taejon, all of Rep. of Korea

[73] Assignee: Shin Poong Pharmaceutical Co., Ltd., Ansan, Rep. of Korea

[21] Appl. No.: 08/959,664

[22] Filed: Oct. 29, 1997

[30] Foreign Application Priority Data

Oct. 31, 1996 [KR] Rep. of Korea ................. 96-51297

[51] Int. Cl.⁷ .................. A61K 31/19; A61K 31/557; A61K 31/195
[52] U.S. Cl. .................................... 514/573; 514/563
[58] Field of Search ....................... 514/563, 573

[56] References Cited

U.S. PATENT DOCUMENTS

| | | | |
|---|---|---|---|
| 5,612,058 | 3/1997 | Schutz et al. | 424/489 |
| 5,646,131 | 7/1997 | Badwan et al. | 514/58 |
| 5,718,917 | 2/1998 | See | 424/450 |
| 5,770,230 | 6/1998 | Teagarden et al. | 424/489 |

OTHER PUBLICATIONS

Bennett et al., *The Journal of Urology*, vol. 146, 1564–1565 (1991).
Zorgniotti et al., *The Journal of Urology*, vol. 133, 39–41 (1985).
Ishii et al., *The Journal of Urology*, vol. 141, 323–325 (1989).
Stackl et al., *The Journal of Urology*, vol. 140, 66–68 (1988).
Nellans et al., *The Journal of Urology*, vol. 138, 52–54 (1987).

*Primary Examiner*—Thedore J. Criares
*Attorney, Agent, or Firm*—Birch, Stewart, Kolasch & Birch, LLP

[57] ABSTRACT

The present invention relates to a stable injectable composition containing prostaglandin $E_1$. More specifically, the present invention relates to a stable injectable composition which is prepared by dissolving prostaglandin $E_1$ in sodium citrate/citric acid buffer solution, filtering the resulting soultion under aseptic condition and then lyophilizing the filtrate, and wherein prostaglandin $E_1$ is stably maintained even when the composition is stored for a long period.

6 Claims, No Drawings

STABLE PROSTAGLANDIN E1-CONTAINING INJECTABLE COMPOSITION

BACKGROUND OF THE INVENTION

1. Field of the Invention

The present invention relates to a stable injectable composition containing prostaglandin $E_1$. More specifically, the present invention relates to a stable injectable composition which is prepared by dissolving prostaglandin $E_1$ in sodium citrate/citric acid buffer solution, filtering the resulting soultion under aseptic condition and then lyophilizing the filtrate, and wherein prostaglandin $E_1$ is stably maintained even when the composition is stored for a long period.

2. Background Art

Prostaglandin $E_1$ has been well known as a vasodilating agent and widely used in the clinical treatment of male sexual functional disorders such as erectile dysfunction, etc., and for induction and acceleration of labor pain and acceleration of delivery in the last stage of pregnancy. However, prostaglandin $E_1$ has the disadvantage of being very unstable in solution and hard to store for a long period when it is prepared as injectable formulation. Furthermore, it is accompanied with serious pain when it is injected.

Therefore, the present inventors have extensively studied preparation of the stable injectable formulation of prostaglandin $E_1$, which does not have the disadvantages as mentioned above, by preparing prostaglandin $E_1$ into injectable formulations by means of various stabilizing agents. As a result, the present inventors have identified that when prostaglandin $E_1$ is prepared in the form of an injectable formulation having a certain composition as mentioned below, a stable prostaglandin $E_1$ injectable composition which is fit for the above purpose can be obtained.

Accordingly, the object of the present invention is to provide a stable injectable composition containing prostaglandin $E_1$.

In addition, another object of the present invention is to provide a stable injectable composition prepared by dissolving prostaglandin $E_1$ in sodium citrate/citric acid buffer solution, filtering the resulting solution under aseptic condition and then lyophilizing the filtrate.

The foregoing has outlined some of the more pertinent objects of the present invention. These objects should be construed to be merely illustrative of some of the more pertinent features and applications of the invention. Many other beneficial results can be obtained by applying the disclosed composition in a different manner, and such modifications are within the scope of the invention.

DISCLOSURE OF THE INVENTION

The present invention relates to a stable injectable composition prepared by dissolving prostaglandin $E_1$ in sodium citrate/citric acid buffer solution, filtering the resulting solution under aseptic condition and then lyophilizing the filtrate.

More specifically, the stable prostaglandin $E_1$ injection according to the present invention can be prepared by dissolving prostaglandin $E_1$ in sodium citrate/citric acid buffer solution having pH value 4.0, filtering the resulting solution under aseptic condition and then lyophilizing the filtrate in a vial.

In order to obtain the more stable formulation, in the injectable composition of the present invention the active component prostaglandin $E_1$ can preferably be used in the form of a clathrate with cyclodextrins, for example, α-cyclodextrin, β-cyclodextrin, or derivatives thereof such as dimethyl-β-cyclodextrin, carboxymethyl-ethyl-β-cyclodextrin, etc. When prostaglandin $E_1$ is clathrated with cyclodextrin, it is suitable to use cyclodextrin in the ratio of 10–50 parts by weight, preferably 30–35 parts by weight, with respect to one part by weight of prostaglandin $E_1$. Prostaglandin $E_1$ is very sensitive to temperature and therefore, cannot be heated during the clathration reaction. Therefore, when cyclodextrin is used in the amount of less than 10 parts by weight with respect to one part by weight of prostaglandin $E_1$, the clathration reaction does not occur, and when cyclodextrin is used in an amount of more than 50 parts by weight with respect to one part by weight of prostaglandin $E_1$, the manufacturing cost increases and the lyophilization takes a long time due to increase in the amount of solvents (including buffer solution, distilled water, etc.) as used. Thus, it is preferable to control the amount of cyclodextrin within the given range as mentioned above.

In the injectable composition of the present invention, sodium citrate/citric acid buffer solution is used in an amount required to adjust the pH value of the composition to about 4.0. In general, it is suitable to use sodium citrate/citric acid buffer solution in the ratio of 130,000–200,000 parts by volume, preferably 160,000–180,000 parts by volume, with respect to one part by weight of prostaglandin $E_1$.

Further, in the injectable composition of the present invention, if appropriate, a conventional pain alleviating agent such as benzyl alcohol, chlorobutanol, etc. can be added in order to alleviate pain when it is injected. In addition, the composition of the present invention can further include pharmaceutically acceptable additives conventionally used for preparation of injectable formulation, for example, isotonizing agent, preservative, excipient for lyophilization (e.g. sugars such as mannitol, lactose, etc.).

The prostaglandin $E_1$ injectable formulation having the above composition according to the present invention, has advantages. Contrary to the prior prostaglandin injections, in which deterioration and decomposition of the active component, prostaglandin $E_1$ occurs. The injectable formulation of the present invention can be stably stored for a long time before use.

The prostaglandin $E_1$ injectable composition according to the present invention can be used in the clinical field, particularly for treatment of male sexual funtional disorder such as erectile dysfunction, on the basis of vasodilating activity as the basic pharmacological activity of prostaglandin $E_1$.

The prostaglandin $E_1$ injectable composition of the present invention can include other active ingredients, especially when it is used for treatment of male sexual functional disorder, such as papaverine and phentolamine in order to potentiate the efficacy of the composition. In view of solubility of papaverine and phentolamine in the injectable solution, they are preferably used in the form of a salt, particularly in the form of papaverine hydrochloride and phentolamine mesylate, respectively. In the composition of the present invention, papaverine and phentolamine can be incorporated by mixing them with prostaglandin $E_1$ and then lyophilization, and alternatively, can be separately preserved in the form of a solution in distilled water for injection and then combined with prostaglandin $E_1$ prior to injection.

After the lyophilized composition containing prostaglandin $E_1$ of the present invention is prepared, it is preferably placed in a vial and then reconstituted prior to injection with a distilled water solution containing additional active components, such as pain alleviating agents, additives, etc.

The present invention is more specifically explained by the following examples and experiment. However, it should be understood that the present invention is not limited to these examples in any manner.

EXAMPLE 1

Preparation of the First Solution 5 mg of prostaglandin $E_1$ was added to 200 ml of sodium citrate/citric acid buffer solution (0.01M, pH 4.0) and dissolved therein with stirring. 23.5 ml of the resulting solution was accurately taken and 3.53 g of mannitol was added thereto and dissolved with stirring. The resulting solution was adjusted to 100 ml with the same buffer solution as used above and then filtered through 0.2 ml membrane filter. The filtrate was dispensed in a sterilized vial by 1 ml and then lyophilized. After lyophilization is completed, the vial was filled with sterilized nitrogen gas and then sealed.

Preparation of the Second Solution 1.76 g of papaverine hydrochloride and 58.8 mg of phentolamine mesylate were added to distilled water for injection and then dissolved with stirring. To the resulting solution was added 1 g of benzyl alcohol and the volume of the solution was adjusted to 100 ml with distilled water for injection. The solution was filtered through 0.2 $\mu$m membrane filter and then dispensed in a sterilized pre-filled syringe by 1 ml.

Just before injection, the injectable formulation is prepared by adding the second solution to the vial of the first solution prepared in the lyophilized form and dissolving the lyophilized first solution, and then administered into corpora cavernosum penis in a suitable amount.

EXAMPLE 2

Preparation of the First Solution 5 mg of prostaglandin $E_1$ was added to 200 ml of sodium citrate/citric acid buffer solution (0.0M, pH 4.0) and dissolved therein with stirring. 23.5 ml of the resulting solution was accurately taken and 1.76 g of papaverine hydrochloride, 58.8 mg of phentolamine mesylate and 3.53 g of mannitol were added thereto and dissolved with stirring. The resulting solution was adjusted to 100 ml with the same buffer solution as used above and then filtered through 0.2 ml membrane filter. The filtrate was dispensed in a sterilized vial by 1 ml and then lyophilized. After lyophilization is completed, the vial was filled with sterilized nitrogen gas and then sealed.

Preparation of the Second Solution 1 g of benzyl alcohol was dissolved in distilled water for injection and the resulting solution was adjusted to 100 ml with distilled water for injection. The solution was filtered through 0.2 $\mu$m membrane filter and then dispensed in a sterilized pre-filled syringe by 1 ml.

Just before injection, the injectable formulation is prepared by adding the second solution to the vial of the first solution prepared in the lyophilized form and dissolving the lyophilized first solution, and then administered into corpora cavemosum penis in a suitable amount.

EXAMPLE 3

Preparation of the First Solution 162 mg of $\alpha$-cyclodextrin was added to 100 ml of sodium citrate/citric acid buffer solution (0.01M, pH 4.0) and dissolved with stirring. To the resulting solution was added 5 mg of prostaglandin $E_1$ and the mixture was stirred at room temperature for about 20 hours to clathrate prostaglandin $E_1$ with $\alpha$-cyclodextrin. After clathration, 11.8 ml of the reaction solution was accurately taken and 3.53 g of mannitol was added thereto and dissolved with stirring. The resulting solution was adjusted to 100 ml with the same buffer solution as used above and then filtered through 0.2 $\mu$m membrane filter. The filtrate was dispensed in a sterilized vial by 1 ml and then lyophilized. After lyophilization is completed, the vial was filled with sterilized nitrogen gas and then sealed.

Preparation of the Second Solution 1.76 g of papaverine hydrochloride and 58.8 mg of phentolamine mesylate were added to distilled water for injection and then dissolved with stirring. To the resulting solution was added 1 g of benzyl alcohol and the volume of the solution was adjusted to 100 ml with distilled water for injection. The solution was filtered through 0.2 $\mu$m membrane filter and then dispensed in a sterilized pre-filled syringe by 1 ml.

Just before injection, the injectable formulation is prepared by adding the second solution to the vial of the first solution prepared in the lyophilized form and dissolving the lyophilized first solution, and then administered into corpora cavernosum penis in a suitable amount.

EXAMPLE 4

Preparation of the First Solution 162 mg of $\alpha$-cyclodextrin was added to 100 ml of sodium citrate/citric acid buffer solution (0.01M, pH 4.0) and dissolved with stirring. To the resulting solution was added 5 mg of prostaglandin $E_1$ and the mixture was stirred at room temperature for about 20 hours to clathrate prostaglandin $E_1$ with $\alpha$-cylcodextrin. After clathration, 11.8 ml of the reaction solution was accurately taken and 1.76 g of papaverine hydrochloride, 58.8 mg of phentolamine mesylate and 3.53 g of mannitol were added thereto and dissolved with stirring.

The resulting solution was adjusted to 100 ml with the same buffer solution as used above and then filtered through 0.2 $\mu$m membrane filter. The filtrate was dispensed in a sterilized vial by 1 ml and then lyophilized. After lyophilization is completed, the vial was filled with sterilized nitrogen gas and then sealed.

Preparation of the Second Solution 1 g of benzyl alcohol was dissolved in distilled water for injection and the resulting solution was adjusted to 100 ml with distilled water for injection. The solution was filtered through 0.2 $\mu$m membrane filter and then dispensed in a sterilized pre-filled syringe by 1 ml.

Just before injection, the injectable formulation is prepared by adding the second solution to the vial of the first solution prepared in the lyophilized form and dissolving the lyophilized first solution, and then administered into corpora cavernosum penis in a suitable amount.

EXAMPLE 5

Preparation of the First Solution 5 mg of prostaglandin $E_1$ was added to 200 ml of sodium citrate/citric acid buffer solution (0.01M, pH 4.0) and dissolved therein with stirring. 23.5 ml of the resulting solution was accurately taken and 1.76 g of papaverine hydrochloride, 58.8 mg of phentolamine mesylate and 3.53 g of mannitol were added thereto and dissolved with stirring. The resulting solution was adjusted to 100 ml with the same buffer solution as used above and then filtered through 0.2 μm membrane filter. The filtrate was dispensed in a sterilized vial by 1 ml and then lyophilized. After lyophilization is completed, the vial was filled with sterilized nitrogen gas and then sealed.

Preparation of the Second Solution 2 g of chlorobutanol was dissolved in distilled water for injection and the resulting solution was adjusted to 100 ml with distilled water for injection. The solution was filtered through 0.2 μm membrane filter and then dispensed in a sterilized pre-filled syringe by 1 ml.

Just before injection, the injectable formulation is prepared by adding the second solution to the vial of the first solution prepared in the lyophilized form and dissolving the lyophilized first solution, and then administered into corpora cavernosum penis in a suitable amount.

COMPARATIVE EXAMPLE 1

Preparation of the First Solution 5 mg of prostaglandin $E_1$ was added to 200 ml of distilled water for injection and dissolved therein with stirring. 23.5 ml of the resulting solution was accurately taken and 1.76 g of papaverine hydrochloride, 58.8 mg of phentolamine mesylate and 3.53 g of mannitol were added thereto and dissolved with stirring. The resulting solution was adjusted to 100 ml with distilled water for injection and then filtered through 0.2 μm membrane filter. The filtrate was dispensed in a sterilized vial by 1 ml and then lyophilized. After lyophilization, the vial was filled with sterilized nitrogen gas and then sealed.

Preparation of the Second Solution 1 g of benzyl alcohol was dissolved in distilled water for injection and the resulting solution was adjusted to 100 ml with distilled water for injection. The solution was filtered through 0.2 μm membrane filter and then dispensed in a sterilized pre-filled syringe by 1 ml.

Just before injection, the injectable formulation is prepared by adding the second solution to the vial of the first solution prepared in the lyophilized form and dissolving the lyophilized first solution, and then administered into corpora cavernosum penis in a suitable amount.

COMPARATIVE EXAMPLE 2

5 mg of prostaglandin $E_1$ was added to 200 ml of sodium citrate/citric acid buffer solution (0.01M, pH 4.0) and dissolved therein with stirring. 23.5 ml of the resulting solution was accurately taken and 1.76 g of papaverine hydrochloride and 58.8 mg of phentolamine mesylate were added thereto and dissolved with stirring. To the resulting solution was added 1 g of benzyl alcohol and the volume of the solution was adjusted to 100 ml with the same buffer solution as used above. The solution was filtered through 0.2 μm membrane filter and then dispensed in a sterilized pre-filled syringe by 1 ml to prepare the injectable formulation.

COMPARATIVE EXAMPLE 3

162 Mg of α-cyclodextrin was added to 100 ml of sodium citrate/citric acid buffer solution (0.01M, pH 4.0) and dissolved with stirring. To the resulting solution was added 5 mg of prostaglandin $E_1$ and the mixture was stirred at room temperature for about 20 hours to clathrate prostaglandin $E_1$ with α-cyclodextrin. After clathration, 11.8 ml of the reaction solution was accurately taken and 1.76 g of papaverine hydrochloride and 58.8 mg of phentolamine mesylate were added thereto and dissolved with stirring. To the resulting solution was added 1 g of benzyl alcohol and the volume of the solution was adjusted to 100 ml with the same buffer solution as used above. The solution was filtered through 0.2 μm membrane filter and then dispensed in a sterilized pre-filled syringe by 1 ml to prepare the injectable formulation.

EXPERIMENT 1

Stability Test

As the test preparation, injections prepared in Examples 1 to 5 according to the present invention and Comparative Examples 1 to 3 were stored at room temperature, 40° C. or 60° C. After a given period, the sample of each test preparation was taken and the content of each component, i.e. prostaglandin $E_1$, papaverine hydrochloride and phentolamine mesylate, in the preparation was measured by liquid chromatography.

The obtained results are shown in the following Table 1.

TABLE 1

| Condition/ period of storage | Example and Compara. Example | prostaglandin $E_1$ | Contents (%) papaverine hydrochloride | pentolamine mesylate |
|---|---|---|---|---|
| room temp./ 12 months | Exam. 1 | 98.8 | 99.2 | 96.7 |
| | Exam. 2 | 98.2 | 100.0 | 99.3 |
| | Exam. 3 | 99.3 | 99.5 | 97.1 |
| | Exam. 4 | 99.0 | 100.0 | 99.5 |
| | Exam. 5 | 98.0 | 100.0 | 99.0 |
| | C. Ex. 1 | 96.4 | 100.0 | 96.8 |
| | C. Ex. 2 | 67.5 | 98.4 | 78.2 |
| | C. Ex. 3 | 75.7 | 98.8 | 80.4 |
| 40° C./ 24 weeks | Exam. 1 | 96.9 | 98.7 | 96.0 |
| | Exam. 2 | 96.5 | 99.8 | 98.1 |
| | Exam. 3 | 97.7 | 98.9 | 96.3 |
| | Exam. 4 | 97.4 | 100.0 | 98.5 |
| | Exam. 5 | 96.2 | 99.6 | 97.7 |
| | C. Ex. 1 | 93.7 | 99.5 | 95.7 |
| | C. Ex. 2 | 32.6 | 97.3 | 62.4 |
| | C. Ex. 3 | 44.5 | 97.6 | 69.5 |
| 60° C./ 20 weeks | Exam. 1 | 95.7 | 97.2 | 95.4 |
| | Exam. 2 | 95.4 | 99.2 | 97.0 |
| | Exam. 3 | 96.2 | 97.3 | 95.8 |
| | Exam. 4 | 96.0 | 99.7 | 97.4 |
| | Exam. 5 | 95.4 | 99.4 | 96.2 |
| | C. Ex. 1 | 88.4 | 99.5 | 95.2 |
| | C. Ex. 2 | 21.5 | 97.4 | 57.4 |
| | C. Ex. 3 | 28.6 | 96.7 | 62.7 |

From the results described in the above Table 1, it is clear that the injectable compositions prepared in Examples 1 to 5 by adjusting prostaglandin $E_1$, solution to pH 4.0 with sodium citrate/citric acid buffer solution and then lyohilizing the solution according to the present invention have a significantly increased stability in comparison to the injections prepared in Comparative Examples 1 to 3. In addition, it can also be confirmed that the use of the clathrate of prostaglandin $E_1$ with α-cyclodextrin (Examples 3 and 4) provides further increase in stability.

What is claimed is:

1. A stable prostaglandin $E_1$-containing injectable composition prepared by a process which comprises:

combining prostaglandin $E_1$, cyclodextrin and a sodium citrate/citric acid buffer solution, filtering the resulting solution under aseptic conditions and then lyophilizing the filtrate;

wherein the sodium citrate/citric acid buffer solution has a pH of about 4.0.

2. The stable prostaglandin $E_1$-containing injectable composition according to claim 1, wherein cyclodextrin is α-cyclodextrin or β-cyclodextrin.

3. The stable prostaglandin $E_1$-containing injectable composition according to claim 1, wherein the cyclodextrin is added to the buffer solution in a ratio of 10–50 parts by weight of cyclodextrin to one part by weight of prostaglandin $E_1$.

4. The stable prostaglandin $E_1$-containing injectable composition according to claim 3, wherein cyclodextrin is added in a ratio of 30–35 parts by weight with respect to one part by weight of prostaglandin $E_1$.

5. A stable prostaglandin $E_1$-containing injectable composition prepared by a process which comprises:

combining cyclodextrin, sodium citrate/citric acid buffer solution, and prostaglandin $E_1$, filtering the resulting solution under aseptic conditions and then lyophilizing the filtrate;

wherein the cyclodextrin is a derivative of α-cyclodextrin or a derivative of β-cyclodextrin, and wherein the buffer solution has a pH of about 4.0.

6. The method of treating a sexual functional disorder comprising administering to a male patient having said disorder, a suitable amount of a prostaglandin $E_1$-containing solution;

wherein the prostaglandin $E_1$-containing solution is prepared just before injection by;

resolvating a stable lyophilized prostaglandin $E_1$-containing injectable composition prepared by a process which comprises combining prostaglandin $E_1$, sodium citrate/citric acid buffer solution, and cyclodextrin, filtering the resulting solution under aseptic conditions and lyophilizing the filtrate, and wherein the buffer solution has a pH of about 4.0.

* * * * *